(12) United States Patent
Jinks et al.

(10) Patent No.: US 11,779,716 B2
(45) Date of Patent: Oct. 10, 2023

(54) METHOD FOR MAKING MEDICINAL DELIVERY DEVICE HAVING MULTI-LAYER COATING

(71) Applicant: KINDEVA DRUG DELIVERY L.P., Saint Paul, MN (US)

(72) Inventors: Philip A. Jinks, Loughborough (GB); Frans A. Audenaert, Kaprijke (BE)

(73) Assignee: Kindeva Drug Delivery L.P., Woodbury, MN (US)

( * ) Notice: Subject to any disclaimer, the term of this patent is extended or adjusted under 35 U.S.C. 154(b) by 738 days.

(21) Appl. No.: 16/635,657

(22) PCT Filed: Aug. 1, 2018

(86) PCT No.: PCT/IB2018/055774
§ 371 (c)(1),
(2) Date: Jan. 31, 2020

(87) PCT Pub. No.: WO2019/025994
PCT Pub. Date: Feb. 7, 2019

(65) Prior Publication Data
US 2021/0121646 A1  Apr. 29, 2021

Related U.S. Application Data

(60) Provisional application No. 62/540,736, filed on Aug. 3, 2017.

(51) Int. Cl.
*A61M 15/00* (2006.01)
*B05D 7/14* (2006.01)
(Continued)

(52) U.S. Cl.
CPC .......... *A61M 15/0066* (2014.02); *B05D 7/14* (2013.01); *B05D 7/52* (2013.01); *C08G 65/336* (2013.01);
(Continued)

(58) Field of Classification Search
CPC ........ B05D 7/14; B05D 7/52; B05D 2202/15; B05D 2202/25; B05D 2506/10;
(Continued)

(56) References Cited

U.S. PATENT DOCUMENTS 3,810,874 A    5/1974  Mitsch
6,149,892 A *  11/2000 Britto ................... B65D 83/752
                                                       424/45

(Continued)

FOREIGN PATENT DOCUMENTS

EP    3034559 A1     6/2016
EP    1343550 B1 *  11/2017  .......... A61M 15/009
(Continued)

OTHER PUBLICATIONS

International Search Report and Written Opinion for PCT/IB2018/055774, issued by the European Patent Office, dated Jan. 29, 2019; 16 pgs.

(Continued)

*Primary Examiner* — William P Fletcher, III
(74) *Attorney, Agent, or Firm* — Mueting Raasch Group (57) ABSTRACT

Methods of making components for a medicinal delivery device are described, in which a base composition comprising a polysulphone is applied to the surface of a component to create a base layer, a primer composition comprising a silane having two or more reactive silane groups separated by an organic linker group is applied to the base layer to create primed surface, and a coating composition comprising an at least partially fluorinated compound is applied to the primed surface. Corresponding coated components and a medicinal delivery device are disclosed.

13 Claims, 3 Drawing Sheets

(51) Int. Cl.
*B05D 7/00* (2006.01)
*C08G 65/336* (2006.01)
*C08G 75/20* (2016.01)

(52) U.S. Cl.
CPC ..... *C08G 75/20* (2013.01); *A61M 2205/0238* (2013.01); *B05D 2202/15* (2013.01); *B05D 2202/25* (2013.01); *B05D 2506/10* (2013.01); *B05D 2518/00* (2013.01); *C08G 2650/48* (2013.01)

(58) Field of Classification Search
CPC ........ B05D 2518/00; B05D 7/56; B05D 7/58; B05D 2518/10; C08G 65/336; C08G 75/20; C08G 2650/48; A61M 15/0066; A61M 15/009; A61M 2205/0238
See application file for complete search history.

(56) References Cited

U.S. PATENT DOCUMENTS

| | | | |
|---|---|---|---|
| 8,430,097 | B2 | 4/2013 | Jinks |
| 8,808,786 | B2 | 8/2014 | Jinks |
| 2009/0214809 | A1 | 8/2009 | al Rohaut |
| 2009/0305051 | A1 | 12/2009 | Corsaro |
| 2010/0242958 | A1 | 9/2010 | Jinks |
| 2017/0081523 | A1 | 3/2017 | Audenaert |
| 2018/0282578 | A1 | 10/2018 | Audenaert |

FOREIGN PATENT DOCUMENTS

| | | | |
|---|---|---|---|
| EP | 1343550 | B1 | 11/2017 |
| WO | WO 02/30848 | A1 | 4/2002 |
| WO | WO 03/049786 | A2 | 6/2003 |
| WO | WO 2005/026236 | A1 | 3/2005 |
| WO | WO 2005/061572 | A1 | 7/2005 |
| WO | WO 2008/045953 | A2 | 4/2008 |
| WO | WO 2009/061891 | A2 | 5/2009 |
| WO | WO 2009/061902 | A2 | 5/2009 |
| WO | WO 2009/061907 | A2 | 5/2009 |
| WO | WO 2010/042784 | A2 | 4/2010 |
| WO | WO 2010/129753 | A1 | 11/2010 |
| WO | WO 2010/129758 | A1 | 11/2010 |
| WO | WO 2010/129783 | A1 | 11/2010 |
| WO | WO 2011/070293 | A1 | 6/2011 |
| WO | WO 2012/173971 | A1 | 12/2012 |
| WO | WO 2015/142894 | A1 | 9/2015 |
| WO | WO 2015/179511 | A1 | 11/2015 |
| WO | WO 2016/054358 | A1 | 4/2016 |
| WO | WO 2017/075018 | A1 | 5/2017 |
| WO | WO-2017075018 | A1 * | 5/2017 ........... A61K 31/439 |

OTHER PUBLICATIONS

International Preliminary Report on Patentability for PCT/IB2018/055774, issued by The International Bureau of WIPO; dated Feb. 13, 2020;11 pgs.

European Examination Report for EP Application No. 18760051.5, issued by the European Patent Office; dated Dec. 10, 2020; 4 pgs.

* cited by examiner

METHOD FOR MAKING MEDICINAL DELIVERY DEVICE HAVING MULTI-LAYER COATING

CROSS REFERENCE TO RELATED APPLICATIONS

This application is a national stage filing under 35 U.S.C. 371 of PCT/IB2018/055774, filed Aug. 1, 2018, which claims the benefit of U.S. Provisional Application No. 62/540,736, filed Aug. 3, 2017, the disclosures of which are incorporated by reference in their entirety herein.

FIELD

The present invention relates to components for medicinal delivery devices, medicinal delivery devices, and methods of making medicinal delivery devices and components.

BACKGROUND

Medicinal delivery devices, including medicinal inhalation devices such as pressurized inhalers, e.g., metered dose pressurized inhalers (MDIs), and dry powder inhalers (DPIs), can be used for delivering medicaments.

Medicinal delivery devices can comprise a plurality of hardware components. In the case of an MDI, these can include gasket seals, metered dose valves (including their individual components, such as ferrules, valve bodies, valve stems, tanks, springs, retaining cups and seals), containers, and actuators. Such components can have internal surfaces that can be in contact with the medicinal formulation during storage or can come in contact with the medicinal formulation during delivery. In medicinal delivery devices, variability in dosing (e.g., from dose to dose in the same device) and variability in dosing between units (e.g., from device to device) is undesirable.

There is a desire to improve dose to dose and unit to unit variability in medicinal delivery devices, including medicinal inhalation devices.

BRIEF SUMMARY

Embodiments of the present invention can provide, in a first aspect, a method of making a component for a medicinal delivery device, the method comprising:

a) providing a component of a medicinal delivery device, b) providing a base composition comprising a polysulphone, c) providing a primer composition comprising a silane having two or more reactive silane groups separated by an organic linker group, d) providing a coating composition comprising an at least partially fluorinated compound, e) applying the base composition to at least a portion of the surface of the component, f) applying the primer composition to at least a portion of the surface of the component after the application of the base composition, g) applying the coating composition to the portion of the surface of the component after application of the primer composition.

Methods according to embodiments of the present invention provide components which, when assembled and in use, may significantly reduce dose to dose variability of medicinal delivery devices. Additionally, such methods provide components which, when assembled and in use, may provide reduced unit to unit variability.

The at least partially fluorinated compound can comprise one or more reactive functional groups, with each one reactive functional group that can be a reactive silane group, for example a hydrolysable silane group or a hydroxysilane group. Such reactive silane groups allow reaction of the partially fluorinated compound with one or more of the reactive silane groups of the primer. Often such reaction can be a condensation reaction.

The reactive silane group may be of formula —Si(R⁰)ₙX₃₋ₙ, wherein R⁰ is a substantially non-hydrolysable group, X is a hydrolysable or hydroxy group and n is 0, 1 or 2.

Thus, in many embodiments the silane having two or more reactive silane groups is of formula $$X_{3-m}(R^1)_m Si-Q-Si(R^2)_k X_{3-k}$$

wherein $R^1$ and $R^2$ are independently selected univalent groups such as C1-C4 alkyl, X is a hydrolysable or hydroxy group, m and k are independently 0, 1, or 2 and Q is a divalent organic linking group.

Q can comprise a 1 to 12 atom chain, such as a substituted or unsubstituted $C_2$ to $C_{12}$ hydrocarbyl chain. Preferably, Q comprises a substituted or unsubstituted $C_2$ to $C_{12}$ alkyl chain.

Useful examples of silanes having two or more reactive silane groups include one or a mixture of two or more of 1,2-bis(trialkoxysilyl) ethane, 1,6-bis(trialkoxysilyl) hexane, 1,8-bis(trialkoxysilyl) octane, 1,4-bis(trialkoxysilylethyl)benzene, bis(trialkoxysilyl)itaconate, and 4,4'-bis(trialkoxysilyl)-1,1'-diphenyl, wherein any trialkoxy group may be independently trimethoxy or triethoxy.

Q may comprise a chain substituted by one or more atoms of N, O, and/or S. Thus, further examples of the silane having two or more reactive silane groups include one or a mixture of two or more of bis(trialkoxysilylpropyl)amine; bis (3-trialkoxysilylpropyl) ethylenediamine; bis (3-trialkoxysilylpropyl) n-methylamine; bis[3-(trialkoxysilyl)propyl]fumarate and N, N-bis (3-trialkoxysilylmethyl) allylamine, wherein any trialkoxy group may be independently trimethoxy or triethoxy.

In preferred embodiments, the silane is such that Q may be of formula $(CH_2)_i\text{-}A\text{-}(CH_2)_j$ wherein A is NR", O, or S; i and j are independently 0, 1, 2, 3 or 4 and wherein R" is H or $C_1$ to $C_4$ alkyl. Even more preferably, Q may be of formula $(CH_2)_i\text{—NH—}(CH_2)_j$ and i and j are each independently 1, 2, 3 or 4. Most preferably i and j are each 3.

The coating solvent can comprise an alcohol or a hydrofluoroether.

If the coating solvent is an alcohol, preferred alcohols are $C_1$ to $C_4$ alcohols, in particular, an alcohol selected from ethanol, n-propanol, or iso-propanol or a mixture of two or more of these alcohols.

If the coating solvent is an hydrofluoroether, it is preferred if the coating solvent comprises a $C_4$ to $C_{10}$ hydrofluoroether. Generally, the hydrofluoroether can be of formula

$$C_gF_{2g+1}OC_hH_{2h+1}$$

wherein g is 2, 3, 4, 5, or 6 and h is 1, 2, 3 or 4. Examples of suitable hydrofluoroethers include those selected from the group consisting of methyl heptafluoropropylether, ethyl heptafluoropropylether, methyl nonafluorobutylether, ethyl nonafluorobutylether and mixtures thereof.

The at least partially fluorinated compound may contain a polyfluoroether moiety, in particular a polyfluoropolyether moiety. More particularly, the polyfluoroether moiety may be a perfluorinated polyfluoroether moiety, even more particularly the polyfluoroether moiety may be a perfluorinated polyfluoropolyether moiety.

The polyfluoropolyether silane may be of formula wherein:
R$^f$ is a polyfluoropolyether moiety;
Q$^1$ is a trivalent linking group;
each Q$^2$ is an independently selected organic divalent or trivalent linking group;
each R$^4$ is independently hydrogen or a C$_{1-4}$ alkyl group;
each X is independently a hydrolysable or hydroxyl group;
R$^5$ is a C$_{1-8}$ alkyl or phenyl group;
v and w are independently 0 or 1, x is 0 or 1 or 2; y is 1 or 2; and z is 2, 3, or 4.

The polyfluoropolyether moiety R$^f$ may comprise perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6. In particular, n may be an integer from 1 to 4, more particularly from 1 to 3. For repeating units including Z the number of carbon atoms in sequence may be at most four, more particularly at most 3. n can be 1 or 2 and Z is an CF$_3$ group, more wherein z is 2, and R$^f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)—, —CF$_2$O(C$_2$F$_4$O)$_p$ CF$_2$—, —(CF$_2$)$_3$O(C$_4$F$_8$O)$_p$(CF$_2$)$_3$—, —CF(CF$_3$)—(OCF$_2$CF(CF$_3$))$_p$O—C$_t$F$_{2t}$—O(CF(CF$_3$)CF$_2$O)$_p$CF(CF$_3$)—, wherein t is 2, 3 or 4 and wherein m is 1 to 50, and p is 3 to 40.

The composition may further comprise a cross-linking agent. The cross-linking agent may comprise a compound selected from group consisting of tetramethoxysilane; tetraethoxysilane; tetrapropoxysilane; tetrabutoxysilane; methyl triethoxysilane; dimethyldiethoxysilane; octadecyltriethoxysilane; 3-glycidoxy-propyltrimethoxysilane; 3-glycidoxy-propyltriethoxysilane; 3-aminopropyl-trimethoxysilane; 3-aminopropyl-triethoxysilane; bis (3-trimethoxysilylpropyl) amine; 3-aminopropyl tri (methoxyethoxyethoxy) silane; N (2-aminoethyl)3-aminopropyltrimethoxysilane; bis (3-trimethoxysilylpropyl) ethylenediamine; 3-mercaptopropyltrimethoxysilane; 3-mercaptopropyltriethoxysilane; 3-trimethoxysilyl-propylmethacrylate; 3-triethoxysilypropylmethacrylate; bis (trimethoxysilyl) itaconate; allyltriethoxysilane; allyltrimethoxysilane; 3-(N-allylamino)propyltrimethoxysilane; vinyltrimethoxysilane; vinyltriethoxysilane; and mixtures thereof.

Thus, in a second aspect, embodiments of the present invention provide, a method of making a component for a medicinal delivery device, the method comprising
a) providing a component of a medicinal delivery device,
b) providing a coating composition comprising an at least partially fluorinated compound,
c) providing a base composition comprising a polysulphone,
d) applying the base composition to at least a portion of the surface of the component to provide a base layer,
e) applying the coating composition to at least a portion of the surface of the component after application of the base layer.

The base composition may comprise a polysulphone and a solvent. In particular, the polysulphone may be in solution in the solvent.

In some embodiments, the polysulphone is a polyethersulphone. Polyethersulphone contains primarily repeating units of the formula below capped by end groups.

The polyethersulphone may be combined with other polymeric materials, such as polyphenylsulphones. In some embodiments, the base composition may consist essentially of a polyethersulphone and a solvent, wherein the polyethersulphone is in solution in the solvent. In some embodiments, the base composition may comprise at least 80%, e.g., at least 90%, at least 95% or even at least 99% polyethersulphone based on the total weight of polymeric materials present in the composition. In some embodiments, there can be greater than 1 weight % polyethersulphone in solution, for example, greater than 2 weight %, greater than 3 weight %, or even greater than 5 weight % polyethersulphone in solution, each of these percentages based on the total weight of base composition. In some embodiments, the polyethersulphone may be in solution in the solvent in an amount of at least 9 weight %, more preferably at least 12 weight %, each of the percentages based on the total weight of the base composition. In some embodiments, the polyethersulphone may be in solution in the solvent in an amount of less than 20 weight %, less than 18 weight %, less than 17.5 weight %, or even less than 15 weight %, each of these percentages based on the total weight of the base composition. Thus, in some embodiments, preferred ranges of polyethersulphone in solution (all in weight % based upon the total weight of the base composition) are: 1 to 20, 2 to 20, 3 to 20, 5 to 20, 1 to 18, 2 to 18, 3 to 18, 5 to 18, 1 to 17.5, 2 to 17.5, 3 to 17.5, 5 to 17.5, 1 to 15, 2 to 15, 3 to 15, 5 to 15, 1 to 10, 2 to 10, 3 to 10, and 5 to 10.

Generally, the solvent comprises cyclopentanone. As used herein, the term "cyclopentanone" refers to unsubstituted cyclopentanone as illustrated by the formula below Thus, in some aspects, the present disclosure provides a base composition comprising polyethersulphone and a solvent, wherein the polyethersulphone is dissolved in the solvent and the solvent comprises cyclopentanone. Other components may or may not be deliberately added to the solvent. Thus, in some embodiments, the solvent may consist essentially of cyclopentanone.

In some embodiments, the solvent comprises cyclopentanone in an amount of at least 70% by volume, based in the total volume of the solvent. For example, in some embodiments, the solvent may comprise cyclopentanone in an amount of greater than 71% by volume, e.g., greater than 75% and even greater than 80% by volume, based on the total volume of solvent. In some embodiments, the solvent can comprise cyclopentanone in large excess for example greater than 85% by volume, e.g., greater than 90%, greater than 95%, or even greater than 99% by volume, each of these percentages based on the total volume of solvent.

In some embodiments, the cyclopentanone may be combined with a miscible cosolvent. In some embodiments, the cosolvent may include a cyclic or heterocyclic ketone, e.g., an aliphatic, cyclic or heterocyclic ketone. For example, in some embodiments, the cosolvent may comprise cyclohexanone.

In some embodiments, the cosolvent may be a 5-membered cyclic or heterocyclic ketone, e.g., a 5-membered aliphatic, cyclic or heterocyclic ketone. In some embodiments, the 5-membered, aliphatic, heterocyclic ketone is saturated. The 5-membered, aliphatic, heterocyclic ketone may include an oxygen atom, a nitrogen atom or a sulphur atom. An example of one with an oxygen atom is γ-butyrolactone. Examples with a nitrogen atom include a pyrrolidone, such as a 2-pyrrolidone. For those with a sulphur atom, an example is tetrahydrothiophenone or a derivative thereof. The 5-membered, aliphatic, heterocyclic ketone may have more than one non-carbon atom in the ring, such as an oxazolidinone, a thiazolidonone, or an imidazolinone.

In some embodiments, the 5-membered, aliphatic, heterocyclic ketone, e.g., a saturated heterocyclic ketone, may be substituted with an alkyl group including such containing one or more heteroatoms. In some embodiments, the alkyl group may contain up to ten carbon atoms. Examples include alkyl substituted 2-pyrrolidone, for example N-alkyl-2-pyrrolidone, e.g., N-methyl-2-pyrrolidone.

In some embodiments, the cosolvent may be a substituted cyclopentanone. In some embodiments, the substituted cyclopentanone may be substituted with alkyl groups such as 2-methyl-cyclopentanone, 3-methyl-cyclopentanone, and 2-ethyl-cyclopentanone. Generally, the alkyl group may contain up to ten carbon atoms. In some embodiments, the substituted cyclopentanones may be substituted with groups containing one or more heteroatoms, such as 2-[1-(5-methyl-2-furyl)butyl]cyclopentanone In some embodiments, the cosolvent may be a linear aliphatic ketone. In some embodiments, the presence of linear aliphatic ketones may hinder the solubility of polyethersulphone. Therefore, in some embodiments, the solvent comprises less than 20 volume %, e.g., less than 10 volume % of a linear aliphatic ketone, based on the total volume of solvent. In some embodiments, the solvent comprises less than 5 volume % of a linear aliphatic ketone, e.g., in some embodiments less than 4 volume %, or even less than 1 volume % of a linear aliphatic ketone, each of these percentages based on the total volume of solvent.

As long as the solvent comprises cyclopentanone, the Hildebrand Solubility Parameter (HSP) may be used to assist in the selection of suitable solvents. Hildebrand Solubility Parameter is a well-known parameter, calculated as the square root of the cohesive energy density of the solvent, where the cohesive energy density is the molar internal energy of vaporization divided by the molar volume. Suitable values may be obtained from Burrell, H., Solubility parameter values, in Polymer Handbook, Brandrup, J. and Immergut, E. H., Eds., John Wiley & Sons-Interscience, New York, 1966, IV-341 (wherein the reference temperature is 25° C.). For mixtures, Hildebrand Solubility Parameter may be calculated by weighting the individual solubility parameters of the constituents according to their volume fraction in the solvent mixture.

In some embodiments, the solubility parameter of the solvent mixture at a reference temperature of 25° C. is greater than 20.5, e.g., at least 20.8, or even at least 21 MPa$^{0.5}$. In some embodiments, the solubility parameter of the solvent mixture at a reference temperature of 25° C. is less than 22.4, e.g., no greater than 22.2, or even no greater than 22 MPa$^{0.5}$. In some embodiments, the solubility parameter of the solvent mixture at a reference temperature of 25° C. is in the range of 20.5 to 22.4 MPa$^{0.5}$, inclusive (i.e., at least 20.5 MPa$^{0.5}$ and no greater than 22.4 MPa$^{0.5}$). In some embodiments, the solubility parameter of the solvent mixture at a reference temperature of 25° C. is in the range of 21 to 22 MPa$^{0.5}$, inclusive.

In some embodiments, the polysulphone is a polyphenylsulphone. Polyphenylsulphone has essentially the formula below capped by end groups.

The structure in square brackets is a repeating unit, repeated n times. Typically, the polyphenylsulphones used in some embodiments have a weight average molecular weight in the range 10,000 to 80,000. Generally, a higher concentration of polyphenylsulphone in solvent-based compositions is possible at the lower end of the molecular weight range. Thus polyphenylsulphones having a weight average molecular weight in the range 10,000 to 30,000 may be advantageous.

The polyphenylsulphone may be combined with other polymeric materials, such as polyethersulphones. In some embodiments, the polyphenylsulphone compositions may consist essentially of a polyphenylsulphone and a solvent, wherein the polyphenylsulphone is in solution in the solvent. Similar solvents to those used for polyethersulphone may be used and selection of solvents based on solubility parameter as described above.

In some embodiments, the polyphenylsulphone may be in solution in the solvent in an amount of less than 20 weight %, less than 18 weight %, less than 17.5 weight %, or even less than 15 weight %, each of these percentages based on the total weight of the composition. In some embodiments, there can be greater than 1 weight % polyphenylsulphone in solution, for example, greater than 2 weight %, greater than 3 weight %, or even greater than 5 weight % polyphenylsulphone in solution, each of these percentages based on the total weight of composition. In some embodiments, the polyphenylsulphone may be in solution in the solvent in an amount of at least 9 weight %, more preferably at least 12 weight %, each of the percentages based on the total weight of the composition. Thus, in some embodiments, preferred ranges of polyphenylsulphone in solution (all in weight % based upon the total weight of the composition) are: 1 to 20, 2 to 20, 3 to 20, 5 to 20, 1 to 18, 2 to 18, 3 to 18, 5 to 18, 1 to 17.5, 2 to 17.5, 3 to 17.5, 5 to 17.5, 1 to 15, 2 to 15, 3 to 15, 5 to 15, 1 to 10, 2 to 10, 3 to 10, and 5 to 10. Desirably the above percentages and ratios of polyphenylsulphone remain in solution without gelling for at least 1 day, e.g., at least 5 days.

Base compositions may be applied to a component surface by any known methods including, e.g., spraying, brushing, dipping or pouring the polyethersulphone composition; and removing at least a portion of the solvent by, e.g., drying. If spraying is employed, it may require separate stages of spraying in different directions relative to the articles to be coated, to allow effective coverage of differently orientated surfaces. Optionally, the coating may subsequently be heated to enhance the flow of the coating composition across the surface of the substrate and/or to drive off solvent. In some embodiments, the resulting polyethersulphone coating is typically in the range 1 μm (microns) to 100 μm thick. In some embodiments, the coating thickness is in the range 1 μm to 25 μm.

In the method, a primer composition may be applied to at least a portion of the surface of the component after application of the base composition and before application of the coating composition. In the method, the base composition, the primer composition and/or the coating composition may be, independently of the application step used for the other, applied by spraying, dipping, rolling, brushing, spreading or flow coating, in particular by spraying or dipping.

In the method, after the step of applying either the base composition, the primer composition or the coating composition, the method may further comprise a step of curing. The curing step may be carried out at an elevated temperature in the range from about 40° C. to about 300° C.

The primer may be cured by evaporating the solvent in a moist environment, as water is responsible for the curing, and may be aided by heat or elevated humidity.

If heat is applied to the primer coating, it is preferable to allow the primer-coated component to cool to room temperature before applying the coating composition to form the top coating.

Typically, a lower curing temperature is used for coating polymers than for coating metals, to avoid deformation of the polymer. However, it has been found that it is not essential to ensure that the primer is cured before applying the top coating, as a final curing can be effectively done to both layers simultaneously, thereby simplifying the manufacturing process. Hence, the primer coat may be allowed to set on the surface such that it is not washed off by the subsequent top coating, by allowing (e.g. by leaving to stand) or causing (e.g. by blowing in a current of air) most of the primer solution solvent to be dispersed.

Coatings applied to valve components, such as plastic stems, metal stems or elastomeric seals, in which the at least partially fluorinated compound is a perfluoropolyether silane according to Formula Ia in which $R^f$ comprises from 20 to 40 linked repeating units confer additional lubricity compared to those with fewer repeating units, and when these are assembled with other component to make up valves, the valves have lower actuation forces.

Formula Ia is:

$$R^f[Q^1-[C(R)_2-Si(Y)_{3-x}(R^{1a})_x]_y]_z \qquad \text{Ia}$$

wherein:
$R^f$ is a monovalent or multivalent polyfluoropolyether moiety;
$Q^1$ is an organic divalent or trivalent linking group;
each R is independently hydrogen or a C1-4 alkyl group;
each Y is independently a hydrolysable group;
$R^{1a}$ is a C1-8 alkyl or phenyl group;
x is 0 or 1 or 2;
y is 1 or 2; and
z is 1, 2, 3, or 4.

In either the first or the second aspect, the surface may be a metal surface, in particular a surface of an aluminium alloy, an iron alloy, or a steel alloy.

In the first aspect, the surface may be a polymer surface. The polymer may be a thermoplastic or thermoset material.

The types of plastics that can thus be coated includes polyalkylenes, polyesters, polyoxymethylene, poly(acrylonitrile-butadiene-styrene) (ABS) or other copolymers comprising monomers of acrylonitrile, butadiene and styrene, such as methylmethacrylate-acrylonitrile-butadiene-styrene (MABS), polycarbonate and nylon, e.g. nylon 6,6 or nylon 6,12. Examples of polyalkylenes are polypropylene and polyethylenes such as low density polyethylene (LDPE), ultra-high molecular weight polyethylene (UHMPE). Polyesters include polyethylene terephthalate (PET) and polybutylene terephthalate (PBT) and copolyester.

Thermosets that may be usefully coated include nitrile elastomer, neoprene elastomer, EPDM and co-vulcanisates of elastomeric polymers with thermoplastic polymers.

Medicinal delivery devices may include inhalers, or other dispensers in which accurate dosing depends on not leaving medicament behind on the device. Examples include a pressurized metered dose inhaler (pMDI), a nebulizer and a dry powder inhaler (DPI). When the device is a pMDI, examples of components include an actuator, an aerosol container, a ferrule, a valve body, a valve stem and a compression spring. For DPIs, examples of components include a powder container, a component used to open sealed powder container, a component that defines at least in part a deagglomeration chamber, a component of a deagglomeration system, a component that defines at least in part a flow channel, a dose-transporting component, a component that defines at least in part a mixing chamber, a component that defines at least in part an actuation chamber, a mouthpiece and a nosepiece.

Components to be coated may be made from one of the above materials, or from assemblies or co mouldings of more than one material including at least one of the above material types.

The primer preferably comprises a linking group with a chain of one to twelve atoms. This may have at least one carbon atom either side of a heteroatom, such as nitrogen, oxygen or sulphur. Particularly useful primers include at least one amine group in the linking group.

Deposition of drug on medicinal delivery device component surfaces may be eliminated when the organic linker comprises one or more amine groups and the at least partially fluorinated compound is a perfluoropolyether silane according to Formula Ia in which y=z=1.

In either the first or the second aspect, the surface of the device or the surface of the component of the device, as applicable, is preferably a surface that is or is intended to come in contact with a medicament or a medicinal formulation during storage or delivery from the medicinal delivery device.

The medicament may comprise or the medicinal formulation may comprise a medicament that may be a drug, vaccine, DNA fragment, hormone or other treatment. Suitable drugs include those for the treatment of respiratory disorders, e.g., bronchodilators, anti-inflammatories (e.g., corticosteroids), anti-allergies, anti-asthmatics, anti-histamines, and anti-cholinergic agents. Therapeutic proteins and peptides may also be employed for delivery by inhalation. Thus the medicament may be selected from the an exemplary group consisting of albuterol, terbutaline, ipratropium, oxitropium, tiotropium, TD-4208, beclomethasone, flunisolide, budesonide, mometasone, ciclesonide, cromolyn sodium, nedocromil sodium, ketotifen, azelastine, ergotamine, cyclosporine, aclidinium, umeclidinium, glycopyrrolate, salmeterol, fluticasone, formoterol, procaterol, indacaterol, TA2005, milveterol, olodaterol, vilanterol, abediterol, omalizumab, zileuton, insulin, pentamidine, calcitonin, leuprolide, alpha-1-antitrypsin, interferon, triamcinolone, salbutamol, pharmaceutically acceptable salts and esters of any of the listed medicaments and mixtures of any of the listed medicaments, their pharmaceutically acceptable salts and esters. For fluticasone, the preferred esters are propionate or furoate; for mometasone, the preferred ester is furoate.

In either the first or the second aspect, the medicinal delivery device is preferably a metered dose inhaler or a dry powder inhaler. Thus, preferably, the component (preferably comprising metal) is a component of a metered dose inhaler and the component is selected from the group consisting of an actuator, an aerosol container, a ferrule, a valve body (that defines a metering chamber), a bottle emptier, a valve stem and a compression spring.

An aerosol formulation used in a metered dose inhaler typically comprises a medicament or a combination of medicaments (as discussed above) and liquefied propellant selected from the group consisting of HFA 134a, HFA 227 and mixtures thereof.

Aerosol formulations may, as desired or needed, comprise other excipients, such as surfactant, a co-solvent (e.g., ethanol), $CO_2$, or a particulate bulking agent. Medicament may be provided in particulate form (e.g. particles generally having a median diameter in the range of 1 to 10 microns) suspended (i.e. dispersed) in the liquefied propellant. Alternatively medicament may be in solution (i.e. dissolved) in the formulation. In the event a combination of two or more medicaments is used, all the medicaments may be suspended or in solution or alternatively one or more medicaments may be suspended, while one or more medicaments may be in solution.

The amount of medicament may be determined by the required dose per puff and available valve sizes, which for MDIs are typically 25, 50 or 63 microlitres, or 100 microlitres.

Pressurized metered dose inhalers including e.g., aerosol containers (in particular metal aerosol containers) whose interior surfaces are coated in accordance embodiments of the invention are particularly advantageous for containing and delivering medicinal aerosol formulations comprising a medicament that is dispersed in said formulation.

In addition embodiments of the present invention are particularly useful in regard to metered dose inhalers including a medicinal aerosol formulation that includes low amounts of surfactant (0.005 wt % with respect to the formulation); or is substantially free (less than 0.0001 wt % with respect to drug) or free of a surfactant. Alternatively or additionally, embodiments, are particularly useful in metered dose inhalers including a medicinal aerosol formulation that contains low amounts of ethanol (less than 5 wt % with respect to the formulation), or is substantially free (less than 0.1 wt % with respect to the formulation) or free of ethanol.

In a third aspect, embodiments of the present invention provide a coated component for a medicinal delivery device comprising a component; a base layer comprising a polysulphone, more particularly a polyethersulphone, wherein the base layer is intermediate the component and a fluorine-containing coating, wherein the fluorine-containing coating comprises two layers, a first polyfluoropolyether-containing layer comprising polyfluoropolyether silane entities of the following Formula Ib:

$$R^f[Q^1\text{-}[C(R)_2\text{—}Si(O\text{—})_{3-x}(R^{1a})_x]_y]_z \qquad \text{Ib}$$

which shares at least one covalent bond with a second non-fluorinated layer comprising entities of the following Formula IIb:

$$(\text{—O})_{3-m-n}(X)_n(R^1)_m Si\text{-Q-}Si(R^2)_k(X)_l(O\text{—})_{3-k-l} \qquad \text{IIb}$$

which in turn is bonded to the base layer; and wherein:

$R^f$ is a monovalent or multivalent polyfluoropolyether segment;

$Q^1$ is an organic divalent or trivalent linking group;

each R is independently hydrogen or a C1-4 alkyl group;

$R^{1a}$ is a C1-8 alkyl or phenyl group;

k, l, m and n are independently 0, 1 or 2, but with the priviso that m+n and k+l are at most 2;

x is 0 or 1 or 2; y is 1 or 2; and z is 1, 2, 3, or 4; wherein $R^1$ and $R^2$ are independently selected univalent groups, X is a hydrolysable or hydroxy group, m and k are independently 0, 1, or 2 and Q is a divalent organic linking group, comprising a substituted $C_2$ to $C_{12}$ hydrocarbyl chain and one or more amine groups.

In one embodiment, the second non-fluorinated layer of Formula IIb is bonded to the base layer by non-covalent intermolecular forces.

Coated components with more specific surface structural features may be determined by the skilled person in respect of more specific process steps described earlier by taking into account the bonding chemistry of this third aspect of embodiments of the invention.

The embodiments of the invention, in its various combinations, either in method or apparatus form, may also be characterized by the following listing of items:

Items

1. A method of making a component for a medicinal delivery device, the method comprising
  a) providing a component of a medicinal delivery device,
  b) providing a base composition comprising a polysulphone,
  c) providing a primer composition comprising a silane having two or more reactive silane groups separated by an organic linker group,
  d) providing a coating composition comprising an at least partially fluorinated compound,
  e) applying the base composition to at least a portion of the surface of the component,
  f) applying the primer composition to at least a portion of the surface of the component,
  g) applying the coating composition to the portion of the surface of the component after application of the primer composition.

2. A method as referred to in item 1, wherein the at least partially fluorinated compound comprises one or more reactive silane groups.

3. A method as referred to in either item for item 2, wherein at least one of the reactive silane groups is a hydrolysable silane group or a hydroxysilane group.

4. A method as referred to in item 3, wherein the or each reactive silane group is of formula —$Si(R^0)_n X_{3-n}$, wherein $R^0$ is a substantially non-hydrolysable group, X is a hydrolysable or hydroxy group and n is 0, 1 or 2.

5. A method as referred to in any one of the preceding items, wherein the silane having two or more reactive silane groups is of formula $$X_{3-m}(R^1)_m Si\text{-Q-}Si(R^2)_k X_{3-k}$$

wherein R¹ and R² are independently selected univalent groups, X is a hydrolysable or hydroxy group, m and k are independently 0, 1, or 2 and Q is a divalent organic linking group.

6. A method as referred to in item 5, wherein Q comprises a 1 to 12 atom chain.

7. A method as referred to in item 6, wherein Q comprises a substituted or unsubstituted $C_2$ to $C_{12}$ hydrocarbyl chain.

8. A method as referred to in item 7, wherein the silane having two or more reactive silane groups is selected from 1,2-bis(trialkoxysilyl) ethane, 1,6-bis(trialkoxysilyl) hexane, 1,8-bis(trialkoxysilyl) octane, 1,4-bis(trialkoxysilylethyl)benzene, bis(trialkoxysilyl)itaconate, and 4,4'-bis(trialkoxysilyl)-1,1'-diphenyl, and combinations thereof, wherein any trialkoxy group may be trimethoxy or triethoxy.

9. A method as referred to in item 7, wherein Q comprises a substituted or unsubstituted $C_2$ to $C_{12}$ alkyl chain.

10. A method as referred to in either item 7 or item 8, wherein the chain is substituted by one or more atoms of N, O, and/or S.

11. A method as referred to in item 9, wherein the silane having two or more reactive silane groups is selected from bis(trialkoxysilylpropyl)amine; bis (3-trialkoxysilylpropyl) ethylenediamine; bis (3-trialkoxysilylpropyl) n-methylamine; bis[3-(trialkoxysilyl)propyl]fumarate and N, N-bis (3-trialkoxysilylmethyl) allylamine, and combinations thereof, wherein any trialkoxy group may be trimethoxy or triethoxy.

12. A method as referred to in item 10, wherein Q is of formula $(CH_2)_i$-A-$(CH_2)_j$— wherein A is NR", O, or S; i and j are independently 0, 1, 2, 3 or 4 and wherein R" is H or $C_1$ to $C_4$ alkyl.

13. A method as referred to in item 12, wherein Q is of formula $(CH_2)_i NH(CH_2)_j$— and i and j are each independently 1, 2, 3 or 4.

14. A method as referred to in any one of items 4 to 13, wherein each X is $OR^3$, each $R^3$ being independently hydrogen, phenyl or $C_1$ to $C_4$ alkyl.

15. A method as referred to in item 14, wherein each $R^3$ is independently methyl, ethyl or propyl.

16. A method as referred to in any one of the preceding items, wherein the coating composition further comprises a coating solvent.

17. A method as referred to in item 16, wherein the coating solvent comprises an alcohol or a hydrofluoroether.

18. A method as referred to in item 17, wherein the alcohol is a $C_1$ to $C_4$ alcohol, in particular, an alcohol selected from ethanol, n-propanol, or iso-propanol.

19. A method as referred to in either item 16 or item 17, wherein the hydrofluoroether is a $C_4$ to $C_{10}$ hydrofluoroether.

20. A method as referred to in item 19, wherein the hydrofluoroether is of formula $$C_g F_{2g+1} OC_h H_{2h+1}$$

wherein g is 2, 3, 4, 5, or 6 and h is 1, 2, 3 or 4.

21. A method as referred to in item 20, wherein the hydrofluoroether is selected from the group consisting of methyl heptafluoropropylether, methyl nonafluorobutylether, ethyl nonafluorobutylether and mixtures thereof.

22. A method as referred to in item 20, wherein the hydrofluoroether comprises ethyl nonafluorobutyl ether.

23. A method as referred to in any one of the preceding items wherein the at least partially fluorinated compound contains a polyfluoroether moiety, in particular a polyfluoropolyether moiety.

24. A method as referred to in item 23, wherein the polyfluoroether moiety is a perfluorinated polyfluoroether moiety, in particular a perfluorinated polyfluoropolyether moiety.

25. A method as referred to in either item 23 or item 24, wherein the polyfluoropolyether moiety is not linked to the functional silane groups via a functionality that includes nitrogen-silicon bond or a sulfur-silicon bond.

26. A method as referred to in any one of items 23 to 25, wherein the polyfluoropolyether moiety is linked to the functional silane groups via a functionality that includes a carbon-silicon bond.

27. A method as referred to in any one of items 23 to 26, wherein in the repeating units of the polyfluoropolyether moiety, the number of carbon atoms in sequence is at most 6.

28. A method as referred to in item 27, wherein in the repeating units of the polyfluoropolyether moiety the number of carbon atoms in sequence is 4 or fewer, more particularly 3 or fewer.

29. A method as referred to in any one of items 23 to 28, wherein the polyfluoropolyether silane is of formula $$R^f Q^1_v [Q^2_w\text{-}[C(R^4)_2\text{—}Si(X)_{3-x}(R^5)_x]_y]_z$$

wherein:
$R^f$ is a polyfluoropolyether moiety;
$Q^1$ is a trivalent linking group;
each $Q^2$ is an independently selected organic divalent or trivalent linking group;
each $R^4$ is independently hydrogen or a $C_{1-4}$ alkyl group;
each X is independently a hydrolysable or hydroxyl group;
$R^5$ is a $C_{1-8}$ alkyl or phenyl group;
v and w are independently 0 or 1, x is 0 or 1 or 2; y is 1 or 2; and z is 2, 3, or 4.

30. A method as referred to in item 29, wherein the polyfluoropolyether moiety $R^f$ comprises perfluorinated repeating units selected from the group consisting of —$(C_n F_{2n} O)$—, —$(CF(Z)O)$—, —$(CF(Z)C_n F_{2n} O)$—, —$(C_n F_{2n} CF(Z)O)$—, —$(CF_2 CF(Z)O)$—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

31. A method as referred to in item 30, wherein n is an integer from 1 to 4 and wherein for repeating units including Z the number of carbon atoms in sequence is at most four.

32. A method as referred to in either item 30 or item 31, wherein n is an integer from 1 to 3 and wherein for repeating units including Z the number of carbon atoms in sequence is at most three.

33. A method as referred to in any one of items 30 to 32, wherein n is 1 or 2 and Z is an $CF_3$ group.

34. A method as referred to in any one of items 29 to 33, wherein z is 2, and $R^f$ is selected from the group consisting of —$CF_2O(CF_2O)_m(C_2F_4O)_p CF_2$—, —$CF(CF_3)O(CF(CF_3)CF_2O)_p CF(CF_3)$—, —$CF_2O(C_2F_4O)_p CF_2$—, —$(CF_2)_3O(C_4F_8O)_p(CF_2)_3$—, —$CF(CF_3)$—$(OCF_2CF(CF_3))_p O$—$C_t F_2$—$O(CF(CF_3)CF_2O)_p CF(CF_3)$—, wherein t is 2, 3 or 4 and wherein m is 1 to 50, and p is 3 to 40.

35. A method as referred to in item 34, wherein $R^f$ is selected from the group consisting of —$CF_2O(CF_2O)_m(C_2F_4O)_p CF_2$—, —$CF_2O(C_2F_4O)_p CF_2$—, and —CF (CF$_3$)—(OCF$_2$CF(CF$_3$))$_p$O—(C$_t$F$_{2t}$)—O(CF(CF$_3$)CF$_2$O)$_p$CF(CF$_3$)—, and wherein t is 2, 3, or 4, and wherein the average value of m+p or p+p or p is from about 4 to about 24.

36. A method as referred to in any one of items 29 to 35, wherein Q$^2$ is selected from the group consisting of —C(O)N(R$^3$)—(CH$_2$)$_a$—, —S(O)$_2$N(R$^3$)—(CH$_2$)$_a$—, —(CH$_2$)$_a$—, —CH$_2$O—(CH$_2$)$_a$—, —C(O)S—(CH$_2$)$_a$—, —CH$_2$OC(O)N(R$^3$)—(CH$_2$)$_a$—, and wherein R$^3$ is hydrogen or C$_{1-4}$ alkyl, and a is 1 to about 25.

37. A method as referred to in any one of items 23 to 36, wherein the weight average molecular weight of the polyfluoropolyether moiety is about 1000 or higher, in particular about 1800 or higher.

38. A method as referred to in any one of the preceding items, wherein the composition further comprises a cross-linking agent.

39. A method as referred to in item 38, wherein the cross-linking agent comprises a compound selected from the group consisting of tetramethoxysilane; tetraethoxysilane; tetrapropoxysilane; tetrabutoxysilane; methyl triethoxysilane; dimethyldiethoxysilane; octadecyltriethoxysilane; 3-glycidoxy-propyltrimethoxysilane; 3-glycidoxy-propyltriethoxysilane; 3-aminopropyl-trimethoxysilane; 3-aminopropyl-triethoxysilane; bis (3-trimethoxysilylpropyl) amine; 3-aminopropyl tri(methoxyethoxyethoxy) silane; N (2-aminoethyl)3-aminopropyltrimethoxysilane; bis (3-trimethoxysilylpropyl) ethylenediamine; 3-mercaptopropyltrimethoxysilane; 3-mercaptopropyltriethoxysilane; 3-trimethoxysilyl-propylmethacrylate; 3-triethoxysilypropylmethacrylate; bis (trimethoxysilyl) itaconate; allyltriethoxysilane; allyltrimethoxysilane; 3-(N-allylamino)propyltrimethoxysilane; vinyltrimethoxysilane; vinyltriethoxysilane; and mixtures thereof.

40. A method as referred to in any one of the preceding items, wherein the base composition further comprises a solvent.

41. A method of making a component for a medicinal delivery device, the method comprising
a) providing a component of a medicinal delivery device,
b) providing a coating composition comprising an at least partially fluorinated compound,
c) providing a base composition comprising a polysulphone,
d) applying the base composition to at least a portion of the surface of the component to provide a base layer,
e) applying the coating composition to at least a portion of the surface of the component after application of the base layer.

42. A method as referred to in any one of the preceding items, wherein the base composition comprises a polyethersulphone.

43. A method as referred to in any one of the preceding items, wherein said surface is a metal surface, in particular a surface of an aluminium alloy, an iron alloy, or a steel alloy.

44. A method as referred to in any one of the preceding items, wherein independently the base composition, the primer composition and/or the coating composition are applied by spraying, dipping, rolling, brushing, spreading or flow coating, in particular by spraying or dipping.

45. A method as referred to in any one of the preceding items, wherein after applying the composition, the method further comprises a step of curing.

46. A method as referred to in item 45, wherein the curing is carried out at an elevated temperature in the range from about 40° C. to about 300° C.

47. A method as referred to in any one of the preceding items, where said surface of the device or said surface of the component of the device, as applicable, is a surface that can come in contact with a medicament or a medicinal formulation during storage or delivery from the medicinal delivery device.

48. A method as referred to in item 47, wherein the medicament comprises or the medicinal formulation comprises a medicament selected from the group consisting of albuterol, terbutaline, ipratropium, oxitropium, tiotropium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, zileuton, insulin, pentamidine, calcitonin, leuprolide, alpha-1-antitrypsin, interferon, triamcinolone, salbutamol and pharmaceutically acceptable salts and esters thereof and mixtures thereof.

49. A method as referred to in any one of the preceding items, where said medicinal delivery device is a metered dose inhaler or a dry powder inhaler.

50. A method as referred to in any one of the preceding items, wherein the component is a component of a metered dose inhaler and the component is selected from the group consisting of an actuator, an aerosol container, a ferrule, a valve body, a valve stem and a compression spring.

51. A medicinal delivery device assembled from at least one component made as referred to in any one of the preceding items.

52. A method as referred in any one of items 30 to 50, wherein the number of linked perfluorinated repeating units is in the range 20 to 40.

53. A method as referred to in any one of items 1 to 39, 44 to 50 and 52, wherein said portion of surface is a polymer surface.

54. A method as referred to in item 53 wherein the component is at least partly made of said polymer.

55. A method as referred to in any one of items 53 and 54, wherein the silane having two or more reactive silane groups is of formula X$_{3-m}$(R$^1$)$_m$Si-Q-Si(R$^2$)$_k$X$_{3-k}$ wherein R$^1$ and R$^2$ are independently selected univalent groups, X is a hydrolysable or hydroxy group, m and k are independently 0, 1, or 2 and Q is a divalent organic linking group, comprising a substituted C$_2$ to C$_{12}$ hydrocarbyl chain and one or more amine groups.

56. A method as referred to in any one of items 53 to 55, wherein the at least partially fluorinated compound is polyfluoropolyether silane of the Formula Ia:

$$R^f[Q^1-[C(R)_2—Si(Y)_{3-x}(R^{1a})_x]_3]_z \quad \text{Ia}$$

wherein:
R$^f$ is a monovalent or multivalent polyfluoropolyether moiety;
Q$^1$ is an organic divalent or trivalent linking group;
each R is independently hydrogen or a C$_1$-4 alkyl group;
each Y is independently a hydrolysable group;
R$^{1a}$ is a C$_1$-8 alkyl or phenyl group;
x is 0 or 1 or 2;
y is 1 or 2; and
z is 1, 2, 3, or 4.

57. A method as referred to in item 56, wherein the polyfluoropolyether moiety R$^f$ comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

58. A method as referred to in item 57, wherein the number of linked perfluorinated repeating units is in the range 3 to 50.

59. A method as referred to in item 58, wherein the number of linked perfluorinated repeating units is in the range 20 to 40.

60. A method as referred to in any one of items 56 to 59, wherein the polyfluoropolyether moiety $R^f$ is terminated with a group selected from the group consisting of $C_nF_{2n+1}$—, $C_nF_{2n+10}$—, $HC_nF_{2n}O$—.

61. A method as referred to in item 60, wherein n=1, 2, 3, 4, 5 or 6.

62. A method as referred to in item 61, wherein the average structure of the polyfluoropolyether moiety $R^f$ is selected from: $C_3F_7O(CF(CF_3)CF_2O)_pCF(CF_3)$—, $CF_3O(C_2F_4O)_pCF_2$—, $C_3F_7O(CF(CF_3)CF_2O)_pCF_2CF_2$—, $C_3F_7O(CF_2CF_2CF_2O)_pCF_2CF_2$—, or $C_3F_7O(CF_2\ CF_2CF_2O)_pCF(CF_3)$—, or $CF_3O(CF_2CF(CF_3)O)_p(CF_2O)G$- (wherein G is $CF_2$, $C_2F_4$—, $C_3F_6$— or $C_4F_8$—), and wherein the average value of p is in the range 3 to 50.

63. A method as referred to in item 62, wherein the polyfluoropolyether moiety $R^f$ is $C_3F_7O(CF(CF_3)CF_2O)_pCF(CF_3)$—.

64. A method as referred to in any one of items 56 to 63, wherein z=1.

65. A method as referred to in any one of items 56 to 64, wherein y=1.

66. A method as referred to in any one of items 56 to 65, wherein $Q^1$ contains one or more heteroatoms selected from the group consisting of sulfur, oxygen, and nitrogen.

67. A method as referred to in item 66 wherein $Q^1$ contains one or more functional groups selected from the group consisting of esters, amides, sulfonamides, carbonyl, carbonates, ureylenes, and carbamates.

68. A method as referred to in item 67 wherein $Q^1$ comprises from 2 to 25 linearly arranged carbon atoms, optionally interrupted by one or more heteroatoms.

69. A method as referred to in item 68 wherein $Q^1$ is substantially stable against hydrolysis and other chemical transformations, such as nucleophilic attack.

70. A method as referred to in item 69 wherein $Q^1$ includes one or more organic linking groups selected from: —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O)S—(CH$_2$)$_k$—, —CH$_2$OC(O)N(R)—(CH$_2$)$_k$—, —CH$_2$OCH$_2$CH(OC(O)NH(CH$_2$)$_3$—)CH$_2$OC(O)NH(CH$_2$)$_3$—C(O)NHCH$_2$CH[OC(O)NH—]CH$_2$OC(O)NH— wherein R is hydrogen or C1-4 alkyl, and k is 2 to about 25, preferably k is 2 to about 15, more preferably k is 2 to about 10.

71. A method as referred to in any one of items 53 to 70, wherein the polymer is a thermoplastic.

72. A method as referred to in item 71, wherein the thermoplastic material is selected from the group consisting of polyolefines, polyesters, polyoxymethylene, nylons, and copolymers comprising acrylonitrile, butadiene and styrene.

73. A method as referred to in item 7. wherein the polyolefine is polyethylene or polypropylene.

74. A method as referred to in any one of items 53 to 70 wherein the polymer is a thermoset material.

75. A coated component for a medicinal delivery device comprising a component; a base layer comprising a polysulphone, wherein the base layer is intermediate the component and a fluorine-containing coating, wherein the fluorine-containing coating comprises two layers, a first polyfluoropolyether-containing layer comprising polyfluoropolyether silane entities of the following Formula Ib:

$$R^f[Q^1\text{-}[C(R)_2\text{—Si(O—)}_{3-x}(R^{1a})_x]_y]_z \qquad \text{Ib}$$

which shares at least one covalent bond with a second non-fluorinated layer comprising entities of the following Formula IIb:

$$(\text{—O})_{3-m-n}X_n(R^1)_m\text{Si-Q-Si}(R^2)_k(X)_l(\text{O—})_{3-k-l} \qquad \text{IIb}$$

which in turn is bonded to the base layer; and wherein:

$R^f$ is a monovalent or multivalent polyfluoropolyether segment;

$Q^1$ is an organic divalent or trivalent linking group;

each R is independently hydrogen or a C1-4 alkyl group;

$R^{1a}$ is a C1-8 alkyl or phenyl group;

k, l, m and n are independently 0, 1 or 2, but with the priviso that m+n and k+l are at most 2;

x is 0 or 1 or 2;

y is 1 or 2; and z is 1, 2, 3, or 4;

$R^1$ and $R^2$ are independently selected univalent groups, X is a hydrolysable or hydroxy group, m and k are independently 0, 1, or 2 and Q is a divalent organic linking group, comprising a substituted $C_2$ to $C_{12}$ hydrocarbyl chain and one or more amine groups.

76. A coated component for a medicinal delivery device as referred to in item 75, wherein the polyfluoropolyether moiety $R^f$ comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

77. A coated component for a medicinal delivery device as referred to in item 76, wherein the polyfluoropolyether moiety $R^f$ is $C_3F_7O(CF(CF_3)CF_2O)_pCF(CF_3)$—, wherein the average value of p is in the range 3 to 50.

78. A coated component for a medicinal delivery device as referred to in any one of items 75 to 77, wherein z=1.

79. A coated component for a medicinal delivery device as referred to in any one of items 75 to 78, wherein y=1.

80. A coated component for a medicinal delivery device as referred to in item 79, wherein the entity of Formula IIb bonds to the base layer by non-covalent intermolecular forces.

81. A coated component for a medicinal delivery device as referred to in any one of items 79 or 80, wherein $Q^1$ includes one or more organic linking groups selected from —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O) S—(CH$_2$)$_k$—, —CH$_2$OC(O)N(R)—(CH$_2$)$_k$—, wherein R is hydrogen or C1-4 alkyl, and k is 2 to about 25, preferably k is 2 to about 15, more preferably k is 2 to about 10.

82. A coated component for a medicinal delivery device as referred to in any one of items 75 to 78, wherein y=2.

83. A coated component for a medicinal delivery device as referred to in any one of items 75 to 82, wherein the base layer comprises a polyethersulphone.

84. A coated component for a medicinal delivery device as referred to in any one of items 82 or 83, wherein $Q^1$ includes as organic linking groups:—

$CH_2OCH_2CH(OC(O)NH(CH_2)_3-)CH_2OC(O)NH(CH_2)_3-$ or $C(O)NHCH_2CH[OC(O)NH-]CH_2OC(O)NH-$.

85. A coated component for a medicinal delivery device as referred in any one of items 75 to 84 wherein the component is a component of a metered dose inhaler.

86. A coated component as referred to in item 85, wherein the component is selected from the group consisting of an actuator, an aerosol container, a ferrule, a valve body, a valve stem and a compression spring.

87. A medicinal delivery device assembled from at least one coated component as referred to in any one of items 75 to 86.

Throughout this specification, the word "inhaler" means a device for delivery of a medicament in fluid (or powder) and does not imply that the device requires inhalation on the part of the patient during delivery. It is known that a medicament may be delivered successfully to the nasal passages by an inhaler without the need for the patient to inhale.

BRIEF DESCRIPTION OF THE DRAWINGS

So that the present specification may be more completely understood, reference is made to the accompanying drawings in which.

DETAILED DESCRIPTION

Figure 1A:
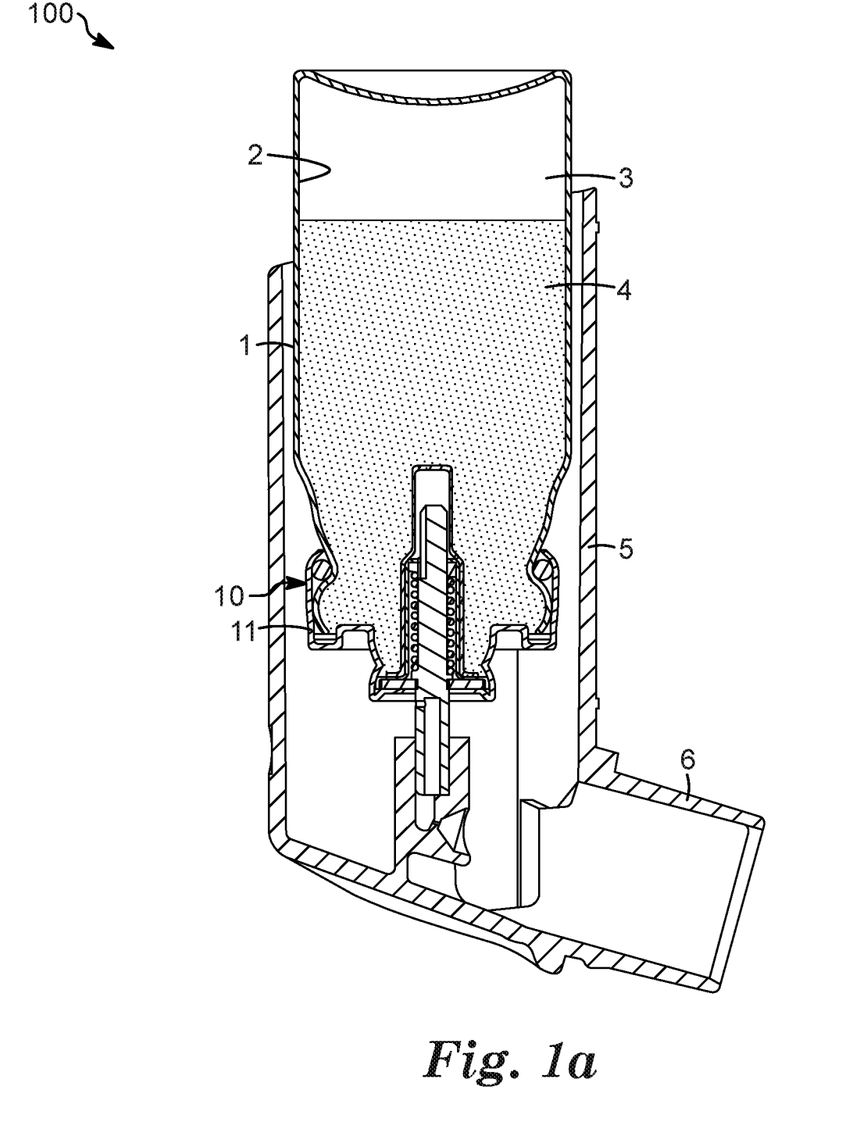
FIG. 1a represents a schematic cross-sectional view of a pressurized metered dose inhaler known in the art and FIG. 1b represents an enlarged view of a portion of the inhaler.

FIG. 1a shows a metered dose inhaler 100, including an aerosol container 1 fitted with a metered dose valve 10 (shown in its resting position). The valve is typically affixed, i.e., crimped, onto the container via a cap or ferrule 11 (typically made of aluminium or an aluminium alloy) which is generally provided as part of the valve assembly. Between the container and the ferrule there may be one or more seals. In the embodiments shown in FIGS. 1a and 1b between the container 1 and the ferrule 11 there are two seals including e. g., an O-ring seal and the gasket seal.

As shown in FIG. 1a, the container/valve dispenser is typically provided with an actuator 5 including an appropriate patient port 6, such as a mouthpiece. For administration to the nasal cavities the patient port is generally provided in an appropriate form (e.g., smaller diameter tube, often sloping upwardly) for delivery through the nose. Actuators are generally made of a plastics material, for example polypropylene or polyethylene. As can be seen from FIG. 1a, the inner walls 2 of the container and the outer walls 101 of the portion(s) of the metered dose valve located within the container define a formulation chamber 3 in which aerosol formulation 4 is contained.

Figure 1B:
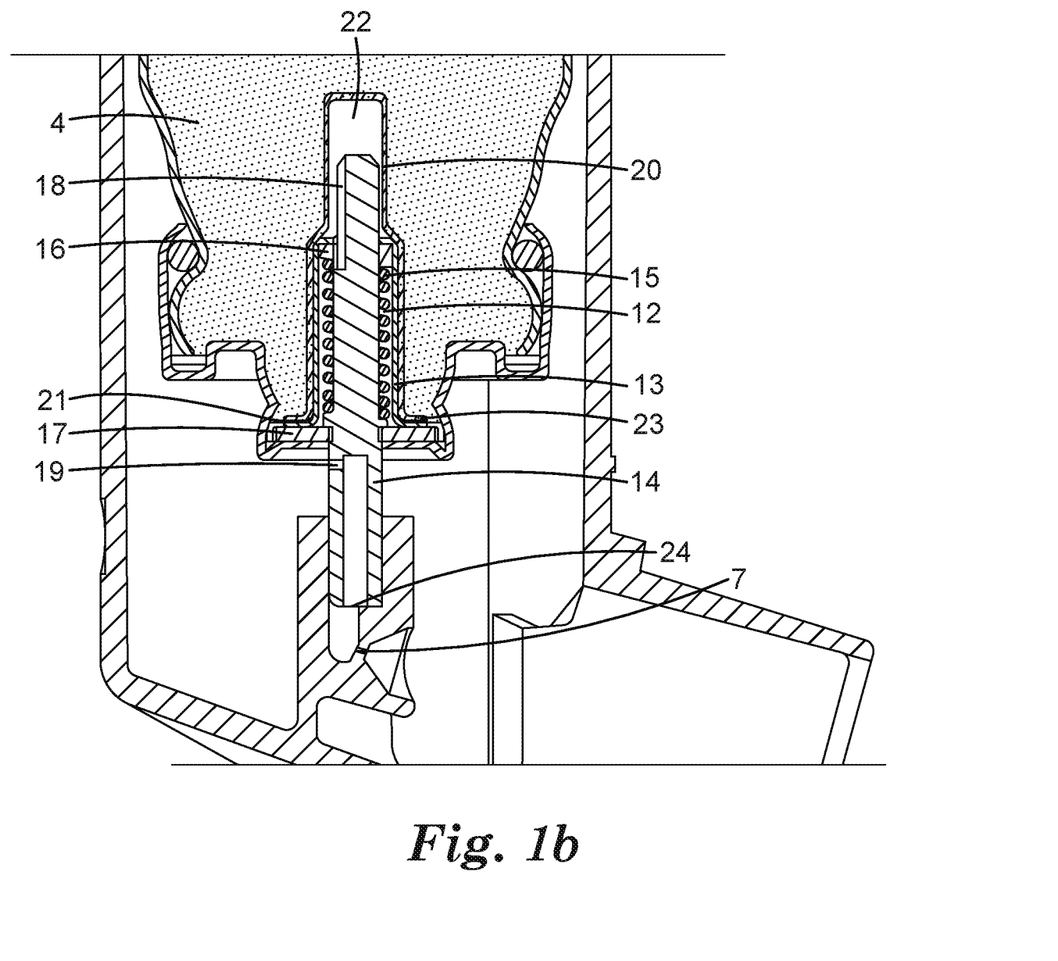

The valve shown in FIG. 1a, and FIG. 1b, includes a metering chamber 12, defined in part by an inner valve body 13, through which a valve stem 14 passes. The valve stem 14, which is biased outwardly by a compression spring 15, is in sliding sealing engagement with an inner tank seal 16 and an outer diaphragm seal 17. The valve also includes a second valve body 20 in the form of a bottle emptier. The inner valve body (also referred to as the "primary" valve body) defines in part the metering chamber. The second valve body (also referred to as the "secondary" valve body) defines in part a pre-metering region or chamber besides serving as a bottle emptier.

Referring to FIG. 1b, aerosol formulation 4 can pass from the formulation chamber into a pre-metering chamber 22 provided between the secondary valve body 20 and the primary valve body 13 through an annular space 21 between the flange 23 of the secondary valve body 20 and the primary valve body 13. To actuate (fire) the valve, the valve stem 14 is pushed inwardly relative to the container from its resting position shown in FIGS. 1a and b, allowing formulation to pass from the metering chamber through a side hole 19 in the valve stem and through a stem outlet 24 to an actuator nozzle 7 then out to the patient. When the valve stem 14 is released, formulation enters into the valve, in particular into the pre-metering chamber 22, through the annular space 21 and thence from the pre-metering chamber through a groove 18 in the valve stem past the inner tank seal 16 into the metering chamber 12.

Figure 2:
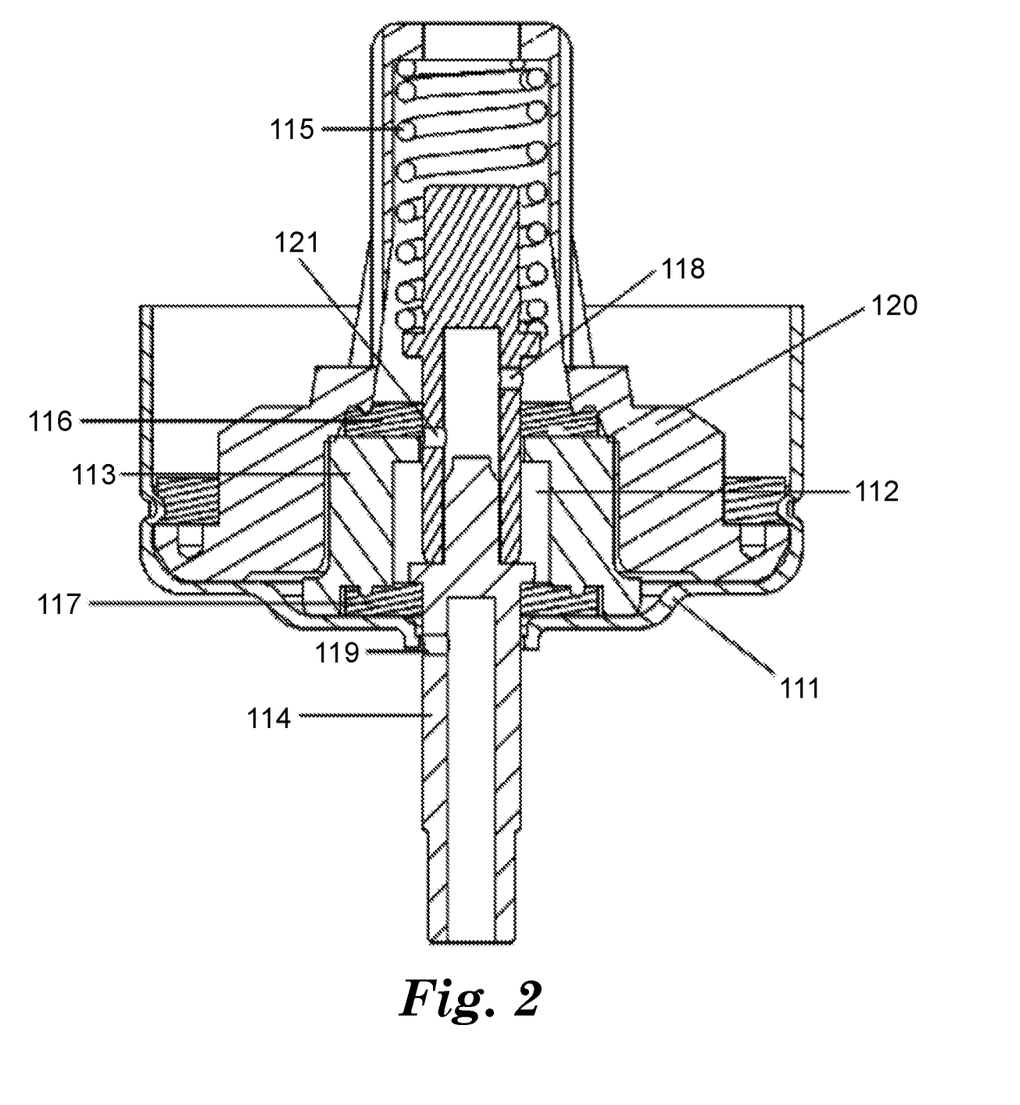
FIG. 2 represents a schematic cross-sectional view of a metered dose valve.

FIG. 2 shows a metered dose aerosol valve different to the one shown in FIGS. 1a, 1b in its rest position. The valve has a metering chamber 112 defined in part by a metering tank 113 through which a stem 114 is biased outwardly by spring 115. The stem 114 is made in two parts that are push fit together before being assembled into the valve. The stem 114 has an inner seal 116 and an outer seal 117 disposed about it and forming sealing contact with the metering tank 113. A valve body 120 crimped into a ferrule 111 retains the aforementioned components in the valve. In use, formulation enters the metering chamber via orifices 121, 118. It's outward path from the metering chamber 112 when a dose is dispensed is via orifice 119.

Depending on the particular metered dose valve and/or filling system, aerosol formulation may be filled into the container either by cold-filling (in which chilled formulation (chilled to temperatures of about −50 to −55° C. for propellant HFA 134a-based formulations) is filled into the container and subsequently the metered dose valve is crimped onto the container) or by pressure filling (in which the metered dose valve is crimped onto the container and then formulation is pressure filled through the valve into the container).

Embodiments of the present invention is further illustrated by the following Examples.

EXAMPLES

Fluorosilane A is a fluorosilane of formula:

$(MeO)_3Si(CH_2)_3OCH_2CF(CF_3)(OCF_2CF(CF_3))_kO(CF_2)_2CF_3$, in which $k$ is approximately 34.

BTMSPA refers to bis(trimethoxysilylpropyl)amine.
Deposition Assay for Canisters
Micronized, non-amorphous salbutamol sulphate that was ultrasonically dispersed in decafluoropentane (1 g in 400 g) was used as the drug deposition agent. Under ambient conditions, an aliquot of the salbutamol sulphate dispersion (0.3 mL) was instilled into each canister using a pipette and the canister was immediately placed on a horizontal rolling mixer (Stuart Scientific model SRT2 operating at 35 rpm)

for three minutes to allow for the dispersion to dry to the surface of the canister. The canisters were then placed in a drying oven for five minutes at 65° C. The dried canisters were individually rinsed with two aliquots of fresh decafluoropentane (each 5 mL) using a five inversion manual shaking regime with one 180 degree shake cycle per second. After the final rinse, the canisters were inverted and then maintained for 15 minutes to allow residual decafluoropentane to evaporate.

The salbutamol sulphate residue remaining in each canister was then assayed. This was performed by dispensing 10 mL of acidified water (deionised water to which 10 mL of 0.1N HCl was added for each 1 liter of deionised water) into each canister. Each canister was capped and then inverted three times to effect dissolution of the salbutamol sulphate residue. The solution in each canister was then assayed using a UV Spectrophotometer (model Lambda 20, PerkinElmer Corporation, Waltham, Mass.) fitted with a sipper cell to sample the solution directly from the canister. Absorbance measurements of the solutions were taken at 276 nm.

Control canisters were prepared from washed, uncoated aluminium canisters. The salbutamol sulphate dispersion was added and dried (as described above), but for the control canisters the rinse step was eliminated. Consequently, the control canisters had a deposited amount of salbutamol sulphate that represented the maximum amount possible for the assay.

Coated canisters that had a low level of salbutamol sulphate deposition following the rinse step were deemed to have a coating with good release/non-stick performance.

The amount of salbutamol sulphate measured for each canister was divided by the corresponding amount measured for the control canisters and the result was expressed as a percentage. Unless otherwise stated, the mean percentage was determined using the results from three canisters.

Example 1

Washing of Canisters

Aluminum canisters (16 mL, used as containers in metered dose inhalers and available from the 3M Company, Clitheroe, UK) were immersed in NOVEC HFE-72DE engineered fluid (a blend of methyl and ethyl nonafluorobutyl ethers with trans-1,2-dichloroethylene, available from the 3M Company, St. Paul, Minn.) at its boiling temperature (43° C.) for seven minutes. The canisters were inverted, drained for two minutes, and then re-immersed in the boiling HFE-72DE for three minutes with added ultrasonic agitation. Next, the canisters were inverted, drained for four minutes, and then air dried for seven minutes.

Preparation of Coated Canisters

Washed aluminium canisters were filled to the brim with a 13 weight percent solution of polyethersulphone (Veradel A-304 NT, available from Solvay Speciality Polymers, Belgium) in cyclopentanone, maintained in the filled state for 60 seconds, and then inverted for five minutes to drain the coating solution. The coated canisters were air dried and then placed in an oven for 30 minutes at 120° C.

The resulting polyethersulphone coated canisters were cooled to 21° C. and then filled to the brim with primer solution (0.1 g of BTMSPA in 84 g of NOVEC HFE-72DE). The canisters were maintained in the filled state for 30 seconds and then inverted to drain the liquid. The canisters were air dried and then placed in an oven for 30 minutes at 140° C.

The resulting primer coated canisters were equilibrated to ambient temperature and humidity, and then filled to the brim with a 0.2 weight percent solution of Fluorosilane A in NOVEC 7200 (a hydrofluoroether solvent blend available from the 3M Company, St. Paul, Minn.). The canisters were maintained in the filled state for 30 seconds and then inverted to drain the liquid. The canisters were air dried and then placed in an oven for 30 minutes at 140° C. The canisters were cooled to ambient temperature and stored under ambient conditions in a resealable polythene bag.

Deposition Assay

The deposition assay was conducted as described above for the canisters prepared according to Example 1. As a comparator, aluminum canisters that were washed, but not coated were also submitted to the deposition test. The results are presented in Table 1.

TABLE 1

| Canister Type | Mean Percent Deposition of Salbutamol Sulphate Relative to Control Canisters |
|---|---|
| Coated Canisters of Example 1 | 0.33% |
| Washed\Uncoated Canisters | 94.7% |

Example 2

Washing of Canisters

Washed 16 mL aluminium canisters were prepared using the washing procedure described in Example 1.

Preparation of Coated Canisters

Washed aluminium canisters were filled to the brim with a 5 weight percent solution of polyphenylsulphone (Radel R5000 NT, available from Solvay Speciality Polymers, Belgium) in cyclopentanone, maintained in the filled state for 60 seconds, and then inverted for 60 seconds to drain the coating solution. The coated canisters were dried by rolling for 16 hours on a horizontal, rolling mixer.

The resulting polyphenylsulphone coated canisters were filled to the brim with primer solution (0.5 g of BTMSPA in 84 g of NOVEC HFE-72DE). The canisters were maintained in the filled state for 30 seconds and then inverted to drain the liquid. The canisters were air dried and then placed in an oven for 30 minutes at 140° C.

The resulting primer coated canisters were filled to the brim with a 0.2 weight percent solution of Fluorosilane A in NOVEC 7200. The canisters were maintained in the filled state for 30 seconds and then inverted to drain the liquid. The canisters were air dried and then placed in an oven for 30 minutes at 140° C. The canisters were cooled to ambient temperature and stored under ambient conditions in a resealable polythene bag.

Deposition Assay

The deposition assay was conducted as described above for the canisters prepared according to Example 2. As a comparator, aluminum canisters that were washed, but not coated were also submitted to the deposition test. The results are presented in Table 2.

TABLE 2

| Canister Type | Mean Percent Deposition of Salbutamol Sulphate Relative to Control Canisters |
|---|---|
| Coated Canisters of Example 2 | 3% |
| Washed\Uncoated Canisters | 95% |

Example 3

Coated canisters prepared according to Example 1 and washed/uncoated aluminum canisters (comparator canisters) were equilibrated for one hour in environmental chambers that were held at a selected temperature and relative humidity (RH). The deposition assay (as described above) was conducted in the environmental chamber. Some of the washed/uncoated canisters were treated according to the procedure for control canisters. Following the rinsing step, canisters were removed from the chamber and assayed using the UV spectrophotometry procedure described above. The results are presented in Table 3 with the mean percent deposition calculated using the results from five canisters.

TABLE 3

| Environmental Chamber Conditions | Mean Percent Deposition of Salbutamol Sulphate Relative to Control Canisters | |
|---|---|---|
| | Coated Canisters of Example 1 | Washed\Uncoated Canisters |
| 21° C., 25% RH | 1% | 65% |
| 21° C., 35% RH | 1% | 69% |
| 21° C., 45% RH | 1% | 77% |
| 21° C., 55% RH | 1% | 89% |
| 21° C., 65% RH | 5% | 92% |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A method of making a component for a medicinal delivery device, the method comprising:
   a) providing a component of a medicinal delivery device,
   b) providing a base composition comprising a polysulphone,
   c) providing a primer composition comprising a silane having two or more reactive silane groups separated by an organic linker group,
   d) providing a coating composition comprising an at least partially fluorinated compound,
   e) applying the base composition to at least a portion of the surface of the component,
   f) applying the primer composition to at least a portion of the surface of the component after the application of the base composition, and
   g) applying the coating composition to the portion of the surface of the component after application of the primer composition.

2. A method as claimed in claim 1, wherein the silane having two or more reactive silane groups is of formula:

wherein $R^1$ and $R^2$ are independently selected univalent groups, X is a hydrolysable or hydroxy group, m and k are independently 0, 1, or 2, and Q is a divalent organic linking group.

3. A method as claimed in claim 2, wherein Q is of formula —$(CH_2)_i$-A-$(CH_2)_j$— wherein A is NR″, O, or S, i and j are independently 0, 1, 2, 3, or 4, and wherein R″ is H or $C_1$ to $C_4$ alkyl.

4. A method as claimed in claim 1, wherein the at least partially fluorinated compound is a polyfluoropolyether silane of formula:

wherein:
   $R^f$ is a polyfluoropolyether moiety;
   $Q^1$ is a trivalent linking group;
   each $Q^2$ is an independently selected organic divalent or trivalent linking group;
   each $R^4$ is independently hydrogen or a $C_{1-4}$ alkyl group;
   each X is independently a hydrolysable or hydroxyl group;
   $R^5$ is a $C_{1-8}$ alkyl or phenyl group;
   v and w are independently 0 or 1, x is 0 or 1 or 2; y is 1 or 2; and
   z is 1, 2, 3, or 4.

5. A method as claimed in claim 4, wherein the polyfluoropolyether moiety $R^f$ comprises perfluorinated repeating units selected from the group consisting of —$(C_nF_{2n}O)$—, —$(CF(Z)O)$—, —$(CF(Z)C_nF_{2n}O)$—, —$(C_nF_{2n}CF(Z)O)$—, —$(CF_2CF(Z)O)$—, and combinations thereof;
   wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

6. A method as referred in claim 5, wherein the number of linked perfluorinated repeating units is in the range 20 to 40.

7. A method as claimed in claim 1, wherein the base composition comprises a polyethersulphone.

8. A method as claimed in claim 1, wherein said surface is a metal surface selected from the group consisting of an aluminium alloy, an iron alloy, and a steel alloy.

9. A method as claimed in claim 1, where said medicinal delivery device is a metered dose inhaler or a dry powder inhaler.

10. A method as claimed in claim 1, wherein the component is a component of a metered dose inhaler and the component is selected from the group consisting of an actuator, an aerosol container, a ferrule, a valve body, a valve stem and a compression spring.

11. A medicinal delivery device assembled from at least one component made as claimed in claim 1.

12. A method as claimed in claim 1, wherein said portion of surface is a polymer surface.

13. A method of making a component for a medicinal delivery device, the method comprising
   a) providing a component of a medicinal delivery device,
   b) providing a coating composition comprising an at least partially fluorinated compound,
   c) providing a base composition comprising polyethersulphone in an amount of less than 20% by weight,
   d) applying the base composition to at least a portion of the surface of the component to provide a base layer,
   e) applying the coating composition to at least a portion of the surface of the component after application of the base layer.

* * * * *

UNITED STATES PATENT AND TRADEMARK OFFICE
CERTIFICATE OF CORRECTION

PATENT NO. : 11,779,716 B2  
APPLICATION NO. : 16/635657  
DATED : October 10, 2023  
INVENTOR(S) : Philip A. Jinks and Frans A. Audenaert Page 1 of 1

It is certified that error appears in the above-identified patent and that said Letters Patent is hereby corrected as shown below:

In the Claims

In Column 22, Line 8, "$R^f Q^1_v [Q^2_w - [C(R^4)_2 - Si(X)_{3-x}(R^5)_x]_3]_z$" should be
-- $R^f Q^1_v [Q^2_w - [C(R^4)_2 - Si(X)_{3-x}(R^5)_x]_y]_z$ --

Signed and Sealed this  
Fifteenth Day of October, 2024

Katherine Kelly Vidal  
*Director of the United States Patent and Trademark Office*